United States Patent [19]
Salamone et al.

[11] Patent Number: 6,063,908
[45] Date of Patent: May 16, 2000

[54] REAGENTS FOR LYSERGIC ACID DIETHYLAMIDE IMMUNOASSAY

[75] Inventors: Salvatore Joseph Salamone, Stockton; Stephen S. Vitone, Piscataway; Robert Sundoro Wu, West Orange, all of N.J.

[73] Assignee: Roche Diagnostics Corporation, Indianapolis, Ind.

[21] Appl. No.: 08/873,955

[22] Filed: Jun. 12, 1997

Related U.S. Application Data

[60] Provisional application No. 60/021,071, Jul. 2, 1996.

[51] Int. Cl.[7] .......................... C07K 17/02; C07D 457/06
[52] U.S. Cl. .......................... 530/405; 530/404; 530/807
[58] Field of Search ............................ 435/188; 530/404, 530/405, 807; 546/69

[56] References Cited

U.S. PATENT DOCUMENTS

| | | | |
|---|---|---|---|
| 4,199,559 | 4/1980 | Ullman et al. | |
| 4,375,414 | 3/1983 | Strahilevitz | |
| 4,754,037 | 6/1988 | Gervais | 546/69 |
| 5,144,030 | 9/1992 | Wang et al. | 546/89 |
| 5,237,057 | 8/1993 | Buechler et al. | 549/390 |
| 5,843,682 | 12/1998 | Sigler et al. | 435/7.6 |

FOREIGN PATENT DOCUMENTS

| | | |
|---|---|---|
| 0 459 387 | 12/1991 | European Pat. Off. |
| 2 282 115 | 3/1976 | France |
| 92/03163 | 3/1992 | WIPO |
| 93/20070 | 10/1993 | WIPO |
| 96/10179 | 4/1996 | WIPO |
| 97/19100 | 5/1997 | WIPO |

OTHER PUBLICATIONS

A.J. McNally et al., J. Analytical Toxicology, vol. 20, pp. 404–408, Oct. 1996.

E. W. Voss, Jr. et al., Psychopharmacologia (Berl.) vol. 26, pp. 140–145, 1972.

A. Castro et al., Research Communications in Chemical Pathology and pharmacology, vol. 6, No. 3, pp. 879–886, Nov. 1973.

A.A. Luderer et al., Bull. New Jersey Acad. Sci., vol. 19, No. 1, pp. 8–10, 1974.

B. Erlanger, Methods in Enzymology, vol. 70, pp. 85–104, 1980.

I. Maggio (editor), Enzyme–immunoassay, Chemical Aspects of Enzyme–immunoassay, Chapter 4, CRC Press, Inc., 1980.

Chemical Abstracts, abstract No. 78869m, 80(15):60 (1974).

Ziegler et al., Biochimica Biophysica Acta., 773;11–12 (1984).

Marzoni et al., Synthesis–Stuttgart, 7:651 (1987).

Ratcliffe, Clin. Chem., 23(2):169–174 (1977).

Taunton–Rigby, Science, 181:165–166 (1973).

Van Vunakis, Proc. Nat. Acad. Sci., 68(7):1483–1487 (1971).

A. Hubbard et al., Anal. Proc., 20:606 (1983).

Primary Examiner—Mary E. Ceperley
Attorney, Agent, or Firm—Gibbons, Del Deo, Dolan, Griffinger & Vecchione

[57] ABSTRACT

The present invention provides hapten derivatives that are useful for the preparation of antigens, antibodies and reagents having superior performance characteristics for use in immunoassays for the detection of LSD and nor-LSD. In the present invention the LSD nucleus is derivatized out of the indole nitrogen to form an aminoalkyl derivative. Derivatives have also been synthesized out of the piperidine nitrogen of the LSD nucleus. The resulting haptens can then be further modified at these functionalized positions for linking to appropriate antigenic or labelling groups to provide reagents for LSD immunoassays having excellent sensitivity and selectivity for both LSD and nor-LSD.

5 Claims, 2 Drawing Sheets

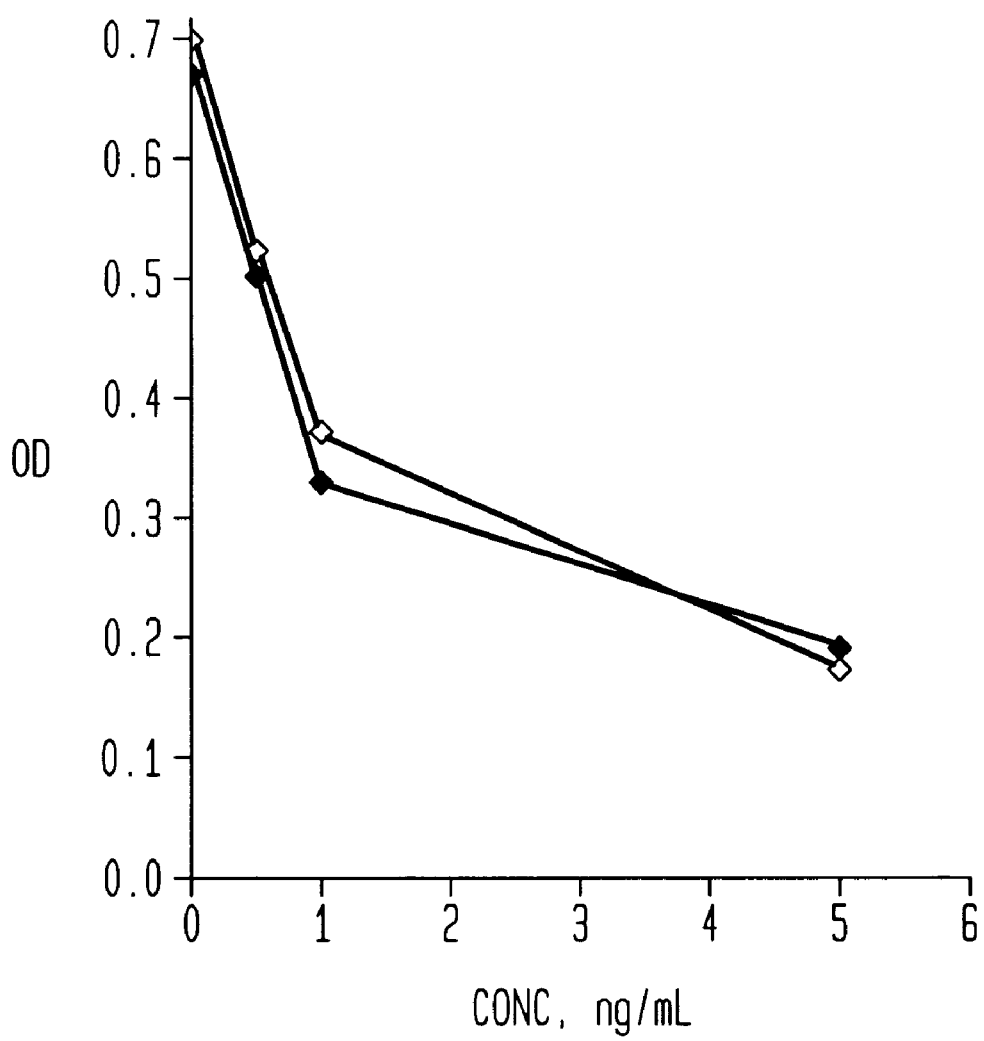

REAGENTS FOR LYSERGIC ACID DIETHYLAMIDE IMMUNOASSAY

This application claims the benefit of U.S. Provisional No. 60/021,071 filed Jul. 2, 1996.

TECHNICAL FIELD

This invention relates to novel lysergic acid diethylamide derivatives and to the use of these derivatives in producing anti-lysergic diethylamide antibodies and to the use of these antibodies as reagents in improved immunoassays for lysergic acid diethylamide and its metabolites in biological fluid samples.

BACKGROUND OF THE INVENTION (+)-Lysergic acid diethylamide, 9,10-didehydro-N,N-diethyl-6-methylergoline-8β-carboxamide, known as LSD, is a hallucinogen which acts on the central nervous system and alters sensory perception. A concentration of from 20 to 80 μg of LSD is sufficient to induce hallucination (Nelson, C. and Foltz, R. Anal. Chem, 64, 1578–1585, 1992). The use of LSD has been and continues to be a problem for drug and law agencies around the world. Current methods used to determine the levels of LSD and its metabolites, for example N-desmethyl LSD (nor-LSD), in biological fluids such as serum and urine include fluorescence spectroscopy, GC/tandem MS, HPLC and radioimmunoassay (RIA). Fluorescence spectroscopy, however, exhibits nonspecific interference and does not distinguish between LSD, its metabolites, and other ergot alkaloids. HPLC results in lower nonspecific interference with antibody binding. However this method is time consuming and not suitable for routine screening of large numbers of samples. Immunoassays offer many advantages over the aforementioned analytical methods, including rapid drug screening and most importantly, high sensitivity.

In immunoassays for drugs such as LSD, a biological fluid sample suspected of containing said drug or its metabolites is contacted with antibodies in the presence of a labeled LSD derivative (label). To the extent that the drug or its metabolites are present in the sample, there will be competition for binding to the antibodies and the amount of the labeled derivative that remains bound will be reduced in proportion to the degree of competition with the drug or its metabolites in the sample.

A fluorescence immunoassay for LSD has been described (B. Law et al., Anal. Proc. 20, 606, 1983). The immunoconjugate that is used to generate antibodies is prepared out of the carboxyl residue of lysergic acid (see e.g., H. Van Vunakis Proc. Nat. Acad. Sci. 68, 1483–1487, 1971) and antibodies derived therefrom would be expected to have high cross-reactivity with a number of ergot alkaloids. The tracer used in this method is produced by conjugating fluoresceinamine to the acid residue of the molecule. The sensitivity of the assay system is in the range of 5–40 ng/mL of LSD. Although this method has the advantage of being rapid, it has a poorer limit of detection than the RIA.

A radioimmunoassay for LSD is described wherein an LSD immunoconjugate is prepared out of the carboxy residue of lysergic acid (see e.g., H. Van Vunakis Proc. Nat. Acad. Sci. 68, 1483–1487, 1971). However, the antibodies derived from the immunoconjugate are not highly specific for LSD. Several ergot alkaloids such as ergosine, ergonovine, ergotamine and methysergide (also known as methylergonovine, Sandoz) are shown to compete for binding to the LSD antibodies, resulting in undesirable false positive results.

Another radioimmunoassay for LSD in serum and urine samples is described (see W. A. Ratcliffe, Clin. Chem. 23(2), 169–174, 1977), wherein the immunoconjugate is prepared via a Mannich type reaction (J. March, Advanced Org. Chem. 4th ed., 900 (1992)), by condensation of LSD and bovine serum albumin (BSA) in the presence of formaldehyde (Tauton-Rigby, Science, 181, 165, 1973). The immunoconjugate produced generates LSD antibodies having low cross-reactivity to a number of ergot alkaloids. The linkage formed in the condensation is derived out of the indole group of the LSD molecule.

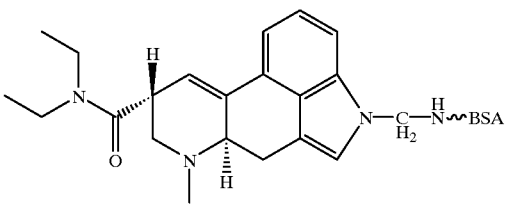

This linkage is similar to an acetal and imidazoline (herein termed an "aminoketal") which serve as the nitrogen protecting groups of indole. As these groups are each susceptible to hydrolysis in an acidic medium, this linkage can also be readily cleaved by hydrolysis in an acidic medium (see e.g., A. J. Stern & J. S. Swenton, J. Org. Chem. 54, 2953 (1989); D. A. Evans, et al., J. Am. Chem. Soc., 103, 5813 (1981); and A. Giannis, et al., Tetrahedron, 44, 7177 (1988)). N,N'-diisopropylidenephenylalanylleucine bearing the "aminoketal" linkage is cleaved simply by heating the material in 10% aqueous solution at 60° C. at neutral pH. (see P. M. Hardy, D. J. Samworth, J. Chem . Soc., Perkin I, 1954 (1977)). Therefore, a method resulting in this unstable linkage is not suitable for making LSD derivatives to be used in preparing haptens and reagents bearing a stable linkage for immunoassay.

Therefore, a non-radioisotopic immunoassay method to rapidly detect LSD and its metabolites, especially in urine samples, is highly desirable. It is also desirable to have an LSD derivative bearing a stable noncleavable linkage from which stable haptens and immunogens can be generated. Furthermore, antibodies used to detect LSD and its metabolites should be highly specific and should not cross-react with other ergot alkaloids.

SUMMARY OF THE INVENTION

The present invention provides hapten derivatives that are useful for the preparation of antigenic, antibody and labelled reagents having superior performance characteristics for use in immunoassays for the detection of lysergic acid diethylamide (LSD) and its metabolites. In one embodiment of the present invention, the LSD nucleus is derivatized out of the indole nitrogen to form an aminoalkyl haptenic derivative. In another embodiment, the derivatives are produced out of the piperidine nitrogen of the nor-LSD molecule. The preferred derivatization is through alkylation forming a functional group which can be further modified for linking to an appropriate linking, antigenic or labelling group to provide stable reagents for the immunoassay.

BRIEF DESCRIPTION OF THE DRAWINGS

FIG. 3 shows the dose response curve for the competition between LSD and 5-[8β-9,10-didehydro-8-[(diethyl-amino)carbonyl]ergolin-6-yl-1,5-dioxopentyl-BSA for binding to anti-LSD antibodies.

DETAILED DESCRIPTION OF THE INVENTION

Figure 1:
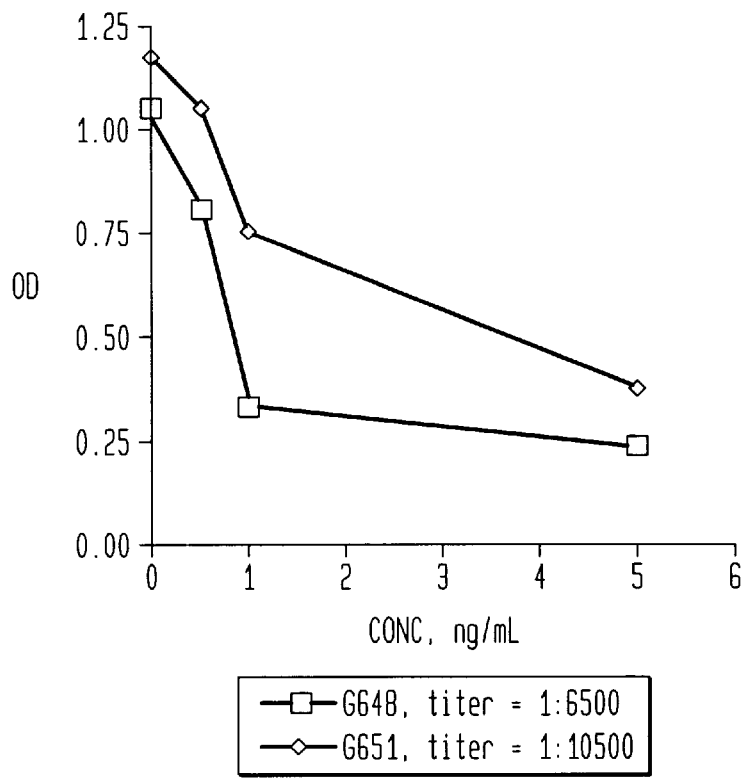
FIG. 1 shows the dose response curve for the competition between LSD and 1-[[[3-carbonyl(1,1'-biphenyl-4-yl]carbonyl]aminopropyl]D-lysergamide-BSA for binding to anti-LSD antibodies.

We describe the synthesis of novel stable LSD derivatives used to prepare LSD haptens, immunogens and LSD-protein conjugates for use in a variety of immunoassay formats.

These compounds are derived from LSD and have the formula

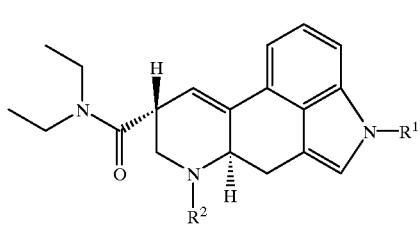

I wherein $R^1$ and $R^2$ are independently selected from H or $R^3R^4$, provided that at least one of $R^1$ and $R^2$ is H but both $R^1$ and $R^2$ are not simultaneously H; $R^3$ is a bond or a saturated straight or branched chain hydrocarbon of 1–10 carbon atoms when $R^4$ is $COR^5$, or $R^3$ is a saturated straight or branched chain hydrocarbon of 1–10 carbon atoms when $R^4$ is $NHR^5$; $R^5$ is selected from H, L or LX; L is a linking group; and X is a detector or carrier molecule bound through L.

The stability of these compounds is provided by the introduction of suitable linkages between the drug moiety and a linking group, carrier proteins or detector molecules.

"Linking groups" are known in the art. They are used to activate, i.e. provide an available site on, a drug derivative for synthesizing a hapten. The use of a linking group may or may not be advantageous or needed depending on the specific hapten and carrier pairs. The selection of an appropriate linking group is within the skill of the art. See e.g., U.S. Pat. Nos. 5,144,030 and 5,237,057. It is well known to those skilled in the art that only combinations of atoms which are chemically compatible can comprise the linking group, e.g. that permit covalent bonding between a carrier and a hapten, resulting in the formation of an amide, thiourea, or thioether linkage depending on the nature of the linking groups used.

Conventional linking groups, including homobifunctional and heterobifunctional linkers, are suitable for coupling to the LSD amine derivatives of the present invention to activate the derivative for further synthesis of the novel LSD haptens and immunogens of the present invention. Examples of suitable bifunctional linkers include dimethylsuberimidate (DMS), N-succinimidyl 3-(2-pyridyldithio)-propionate (SPDP), diisothiocyanatobenzene, 4-isothiocyanatobenzoylchloride and m-maleimidobenzoyl-N-hydroxysuccinimide ester (MBS) (Pierce, Rockford, Ill.).

As used herein, the term "carrier molecule" includes those materials which have the property of independently eliciting an immunogenic response in a host animal and which can be covalently coupled to the hapten derivatives described herein. Suitable carrier materials include, for example, proteins natural or synthetic polymeric compounds such as polypeptides, and the like. Particularly preferred carrier materials are proteins.

The identity of the protein materials utilized in the preparation of an immunogen of the instant invention is not critical. Examples of suitable proteins useful in the practice of this invention include bovine thyroglobulin (BTG), bovine gamma globulin, and bovine serum albumin (BSA). It is generally preferred, but not necessary, that proteins be utilized which are foreign to the animal hosts in which the antibodies against LSD or its metabolites and derivatives are to be elicited.

By attaching the hapten derivative of the present invention to a group consisting of an immunogenic carrier material, antisera and polyclonal antibodies, as well as monoclonal antibodies can be produced and isolated which are useful reagents for immunoassays for the detection of LSD and its metabolites. Carriers are typically used because low molecular weight compounds (here, the hapten) are generally not immunogenic when administered by themselves. When a carrier is conjugated to a hapten and the conjugate is used as an immunogen, antibodies can be generated to the hapten that would not be produced by immunization with hapten alone.

The derivatives, such as the haptens, can also be coupled to a variety of tracer, detection or carrier molecules by methods well known in the art to provide a variety of reagents useful in different immunoassay formats. For detection, there can be attached detector molecules such as fluorophores, for example fluorescein to produce tracers, or radiolabelled or chemiluminescent groups. The hapten can be bound to microparticles including colored latex for use on spectrophotometric or direct optical detection formats such as latex agglutination or chromatographic strip tests. The attached group may also be an "indirect" detection molecule such as an energy transfer partner, enzyme or other group which is detected by further chemical reaction.

In the present invention, the LSD hapten derivatives are activated and coupled to proteins, for example carrier proteins such as BSA or BTG, to form immunogens. Additionally, these carrier groups are used to form reagents for immunoassay, i.e. tethers for the attachment of the haptens to solid matrices, or labelling groups such as microparticles, radioactive labels etc., forming "label-conjugates". The "label-conjugates" are used as reagents in immunoassays or in ELISA microtiter plate assays for competing with the drug for binding to antibodies. The label-conjugate can be used, for example, in certain assay formats to coat microtiter assay plates.

In one embodiment of the present invention, we have unexpectedly found that the novel derivatives of formula I can be prepared by introducing a spacer arm out of the indole nitrogen of the LSD moiety to produce LSD derivatives having the formula

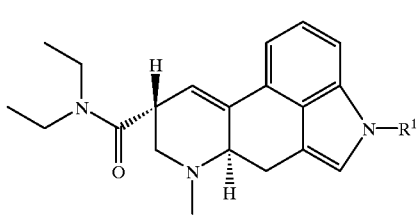

II wherein $R^1$ is $R^3R^4$; $R^3$ is a saturated straight or branched chain hydrocarbon of 1–10 carbon atoms and $R^4$ is $NHR^5$;

$R^5$ is selected from H, L or LX; L is a linking group; and X is a detector or carrier molecule bound through L. Preferably L is selected from the group consisting of dimethylsuberimidate, N-succinimidyl 3-(2-pyridyldithio) propionate, diisothiocyanatobenzene, 4-isothiocyanatobenzoylchloride and m-maleimidobenzoyl-N-hydroxysuccinimide ester; and X is a carrier molecule, for example, BSA or BTG.

The preferred method for introducing a spacer arm or spacer to the LSD molecule is through alkylation. Spacers are known in the art and are commonly used to provide additional spacing between a hapten and the carrier molecule. Typical spacers will be from 1–20 carbon atoms and can have 0–10 heteroatoms, for example N, O, COOH or S, and may be straight or branched chain. In the present invention, the spacer was introduced onto the LSD molecule via a suitable alkylation agent, selected from, for example, 4-bromoethylbutyrate, iodoethylacetate, 4-bromomethylbenzoic acid, acrylic acid and acryloin. Alkylation of the indole nitrogen is described using alkylating agents such as methyl iodide or n-butylbromide (see E. Santaniello, *Synthesis,* 617 (1979)); benzylation with benzyl iodide (see Y. Kiguawa, *Synthesis,* 421(1981); N-alkylation of 3-acetylindole with allylbromide (see T. Kurihara, *Synthesis-Stuttgart* 4:396(1987); N-alkylation of dihydrolysergic acid at the indole nitrogen with cyclopentyl tosylate using powder KOH in DMSO (see G. Marzoni and W. L Garbrecht, *Synthesis-Stuttgart,* 7:651(1987); preparation of N-methyl derivative of ergoline (see U.S. Pat. No. 4,754,037). Using such conditions (e.g., G. Marzoni and W. L Garbrecht, *Synthesis-Stuttgart,* 7:651 (1987)) which included alkylation with N-(4-iodobutyl)phthalimide on the indole nitrogen center, we were not able to obtain an alkylated LSD derivative. None of the known methods describes the successful derivatization of LSD at the indole nitrogen from which position the stable LSD derivatives of the present invention are generated.

In the present invention, known alkylating agents such as 4-(bromomethyl)t-butyl benzoate, haloalkyl nitrile, bromoacetonitrile and bromo-t-butyl acetate can be used to provide the desired stable linkage. In order to alkylate at the indole nitrogen, we found it necessary to first generate an anion at the indole nitrogen. The anion was then quenched with an appropriate alkylating agent to form an amine.

In a preferred method for generating the LSD derivatives, shown in Scheme I below, the indole nitrogen anion was generated with n-butyl lithium in the presence of hexamethyl phosphoramide (HMPA) or, preferably, N,N'-dimethylpropylene urea (DMPU) in lieu of the more toxic HMPA. The resulting anion was then quenched with N-(4-iodobutyl)phthalimide yielding compound 4. Deprotection of the phthalimide in anhydrous hydrazine provided the functionalized LSD derivative 5 which was used for generating the corresponding hapten and immunogen.

We selected the bifunctional linker 4-isothiocyanatobenzoyl chloride, compound 6, (see K. Ziegler, M. Frimer, S. Mullner and H. Fasold, *Biochem. Biophys. Acta,* 773:11–22 (1984)) to convert the amine to the hapten 7. This hapten was further transformed to the corresponding LSD immunogen 8 as illustrated in Scheme I below.

SCHEME I

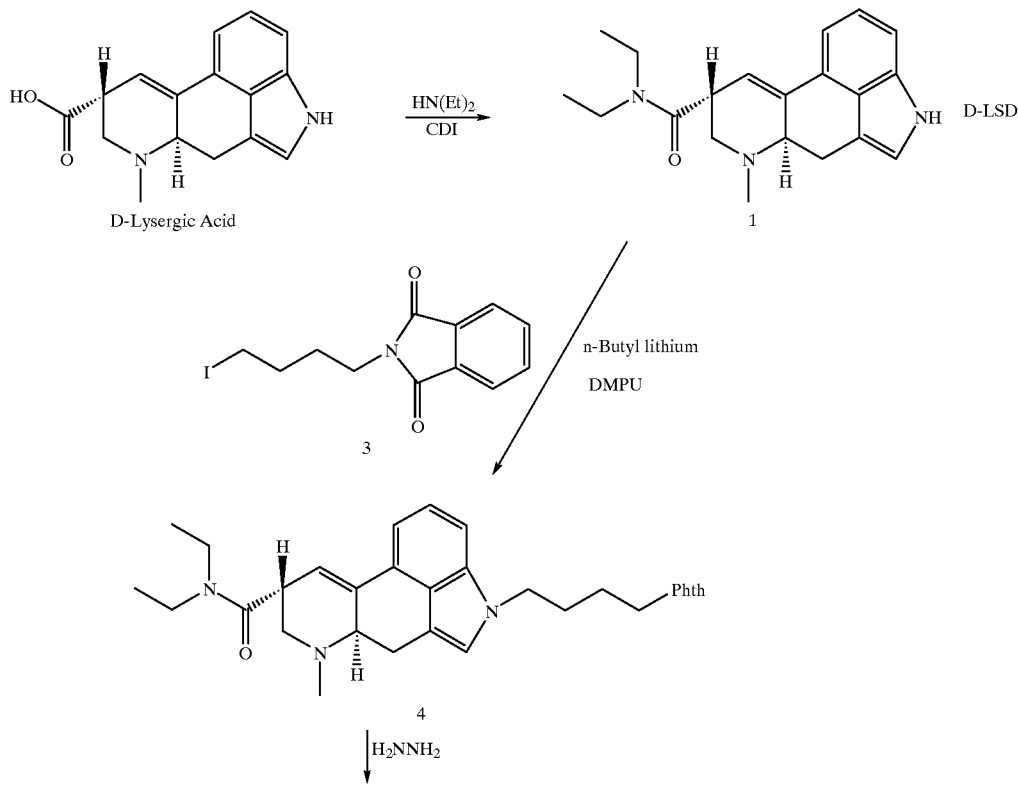

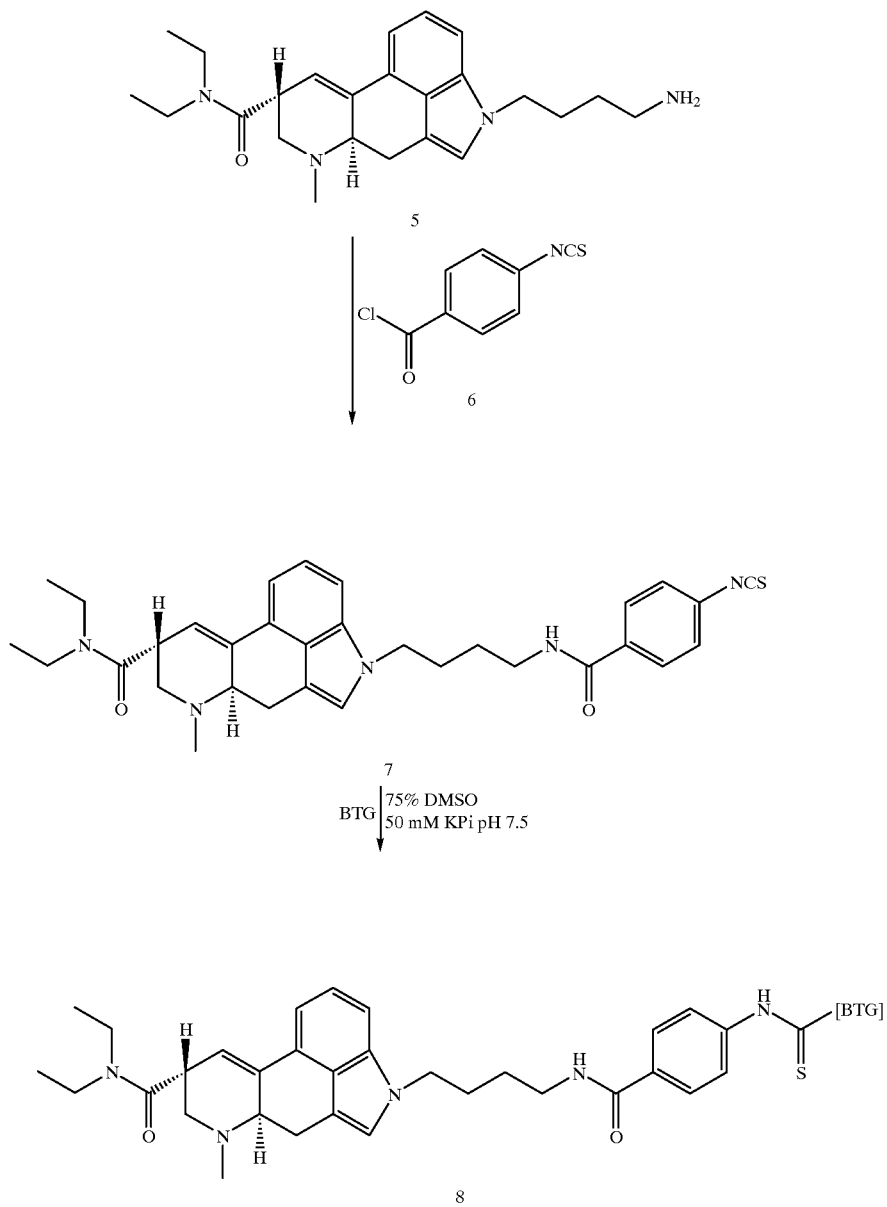

Immunogen 8 was then used to generate anti-LSD antibodies, designated G648 and G651, according to the method described in Example 26.

In an alternate synthesis, the LSD derivatives were activated to form stable hapten labels and label-conjugates for use in an immunoassay to detect LSD and its metabolites. LSD is sensitive to light and alkaline pH. At a pH above 7, the molecule undergoes an epimerization at the C-8 position, resulting in partial formation of iso-LSD. Under prolonged exposure to light, LSD is oxidized at the C-9 position resulting in the loss of the olefin group. Therefore, it is desirable to prepare activated derivatives that generate stable hapten labels and label-conjugates which are able to withstand long-term storage, a paramount consideration in formulating reagents for convenient use in a production environment.

The synthesis of the novel hapten 13 is illustrated in SCHEME II, below. For the synthesis of the haptens, the indole nitrogen was quenched with N-(3-iodopropyl) phthalimide and treated with anhydrous hydrazine, yielding amine 10 to which a linking group was attached. Conventional linking groups, such as isothiocyanatobenzoyl chloride, DSS and SPDP, are suitable for the synthesis of the haptens. The most preferred linking group, however, was a heterobifunctional linker 12 which was found to provide an overall good stability to the compounds. Coupling of the linking group 12 with the LSD-amine 10 in an anhydrous condition yielded the hapten 13.

SCHEME II
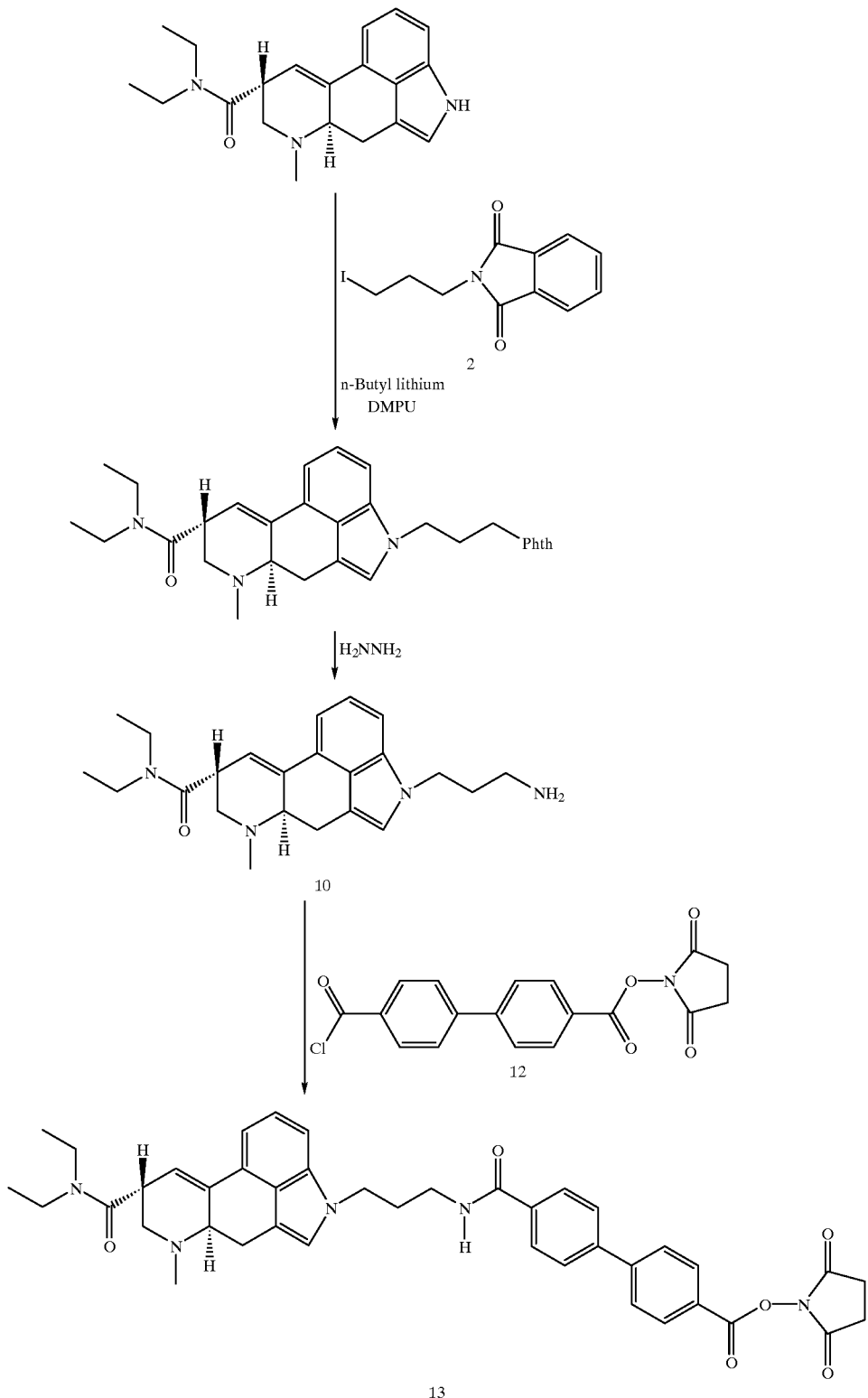
The novel hapten 13 was coupled to BSA as described in example 14 to provide label-conjugate 14, shown below.

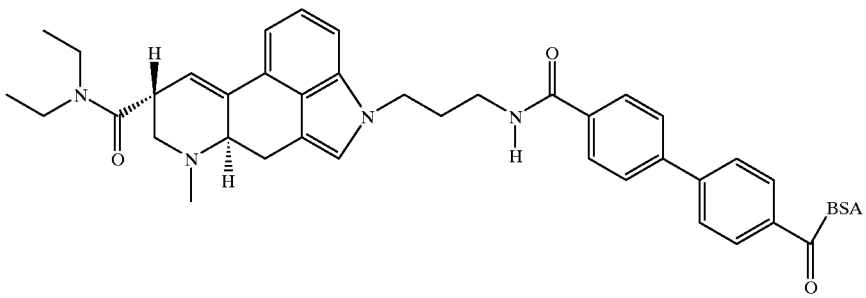

14

The novel reagents were tested in an ELISA immunoassay as described in Example 27. The N-indole derived LSD-BSA label-conjugate 14 containing the biphenyl linker was used to compete against known concentrations of LSD for binding to the anti-LSD antibodies, G648 and G651, raised against the LSD immunogen 8. The data shown in Example 27 resulted in the dose response curve shown in FIG. 1.

The curve in FIG. 1 demonstrates that the anti-LSD antibodies raised against the LSD immunogen 8 bind to the LSD label-conjugate 14. Free LSD competes with the BSA label-conjugate 14 for binding with the anti-LSD antibodies such that the presence of LSD results in a decrease or inhibition of the antibody-antigen binding. The results demonstrate novel LSD label-conjugate 14 can be used as a reagent in the ELISA for the determination of LSD in combination with LSD derivatives having different linking groups.

Figure 2:
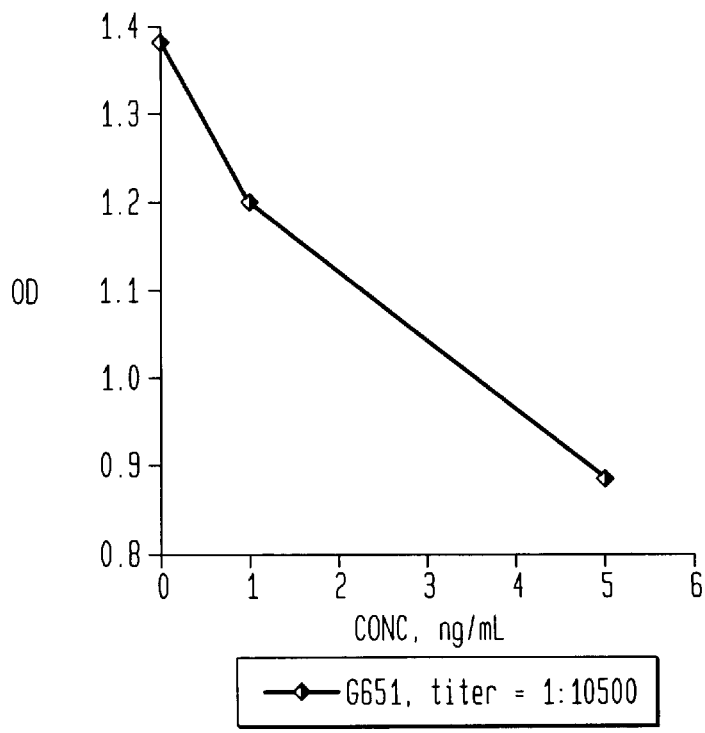
FIG. 2 shows the dose response curve for the competition between nor-LSD and 1-[[[3-carbonyl(1,1'-biphenyl-4-yl]carbonyl]amino-propyl]D-lysergamide-BSA for binding to an anti-LSD antibody.

The two antibodies raised against the LSD immunogen 8, G648 and G651, were shown to also bind to a major metabolite of LSD, nor-LSD. FIG. 2 provides the curve generated from an ELISA microtiter plate assay, as described in Example 27, using nor-LSD as the standard.

The inhibition curve of FIG. 2, generated from data provided in Example 27, demonstrates that LSD derivative 14, prepared out of the indole nitrogen of the LSD molecule, competes in a dose dependent manner with nor-LSD for binding to the antibodies generated from the LSD immunogen 8 and is therefore useful in an immunoassay for the detection of nor-LSD.

In addition to the novel LSD derivatives described above, which are derived out of the indole nitrogen of LSD, we have also synthesized another class of LSD derivatives out of the piperidine nitrogen of the LSD molecule to produce an LSD derivative having the formula

III

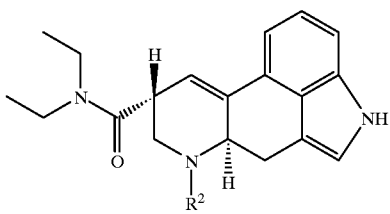

wherein $R^2$ is $R^3R^4$; $R^3$ is a bond or is a saturated straight or branched chain hydrocarbon of 1–10 carbon atoms when $R^4$ is $COR^5$, or $R^3$ is a saturated straight or branched chain hydrocarbon of 1–10 carbon atoms when $R^4$ is $NHR^5$; $R^5$ is selected from L or LX; L is a linking group; and X is a detector or carrier molecule bound through L.

L is selected from the group consisting of dimethylsuberimidate, N-succinimidyl 3-(2-pyridyldithio)propionate, diisothiocyanatobenzene, 4-isothiocyanatobenzoylchloride and m-maleimidobenzoyl-N-hydroxysuccinimide ester; and X is a carrier molecule, for example, BSA or BTG. These derivatives were used to synthesize additional haptens and immunogens useful as reagents in a variety of LSD immunoassay formats, including a microtiter plate format.

The synthesis of the derivatives out of the piperidine nitrogen requires the formation of nor-LSD prior to derivatization. Scheme III, below, illustrates the synthesis of nor-LSD 16, and LSD hapten 19, LSD immunogen 20 and label-conjugate 21 formed out of the piperidine nitrogen. For this synthesis, LSD was treated with BrCN to yield the cyano derivative 15, which upon further treatment with Zn in HOAc provided nor-LSD 16. Nor-LSD was coupled to the bifunctional linker 18 in the presence of triethylamine (TEA) to yield the piperidine-N derived LSD hapten 19, which was further coupled to BSA to provide the most-preferred label-conjugate 21. See Scheme III below. This conjugate proved to be useful as another reagent in the LSD immunoassay when used together with the antibodies raised from immunogen 8. In the ELISA described in Example 27, a dose response curve was generated using LSD as the standard. FIG. 3 illustrates the inhibition curve, generated from data shown in Example 27, of LSD by the BSA label conjugate 21.

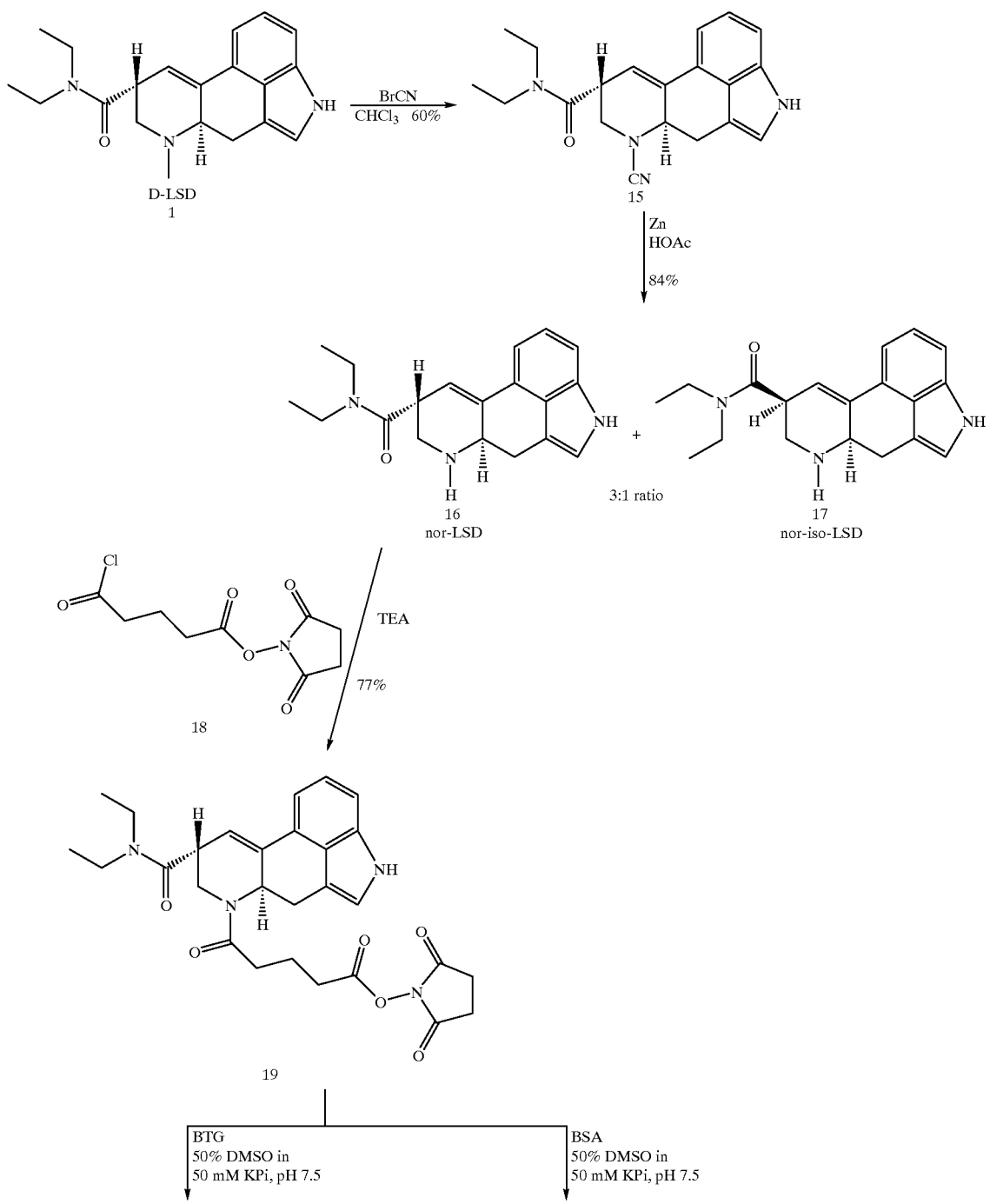
SCHEME III

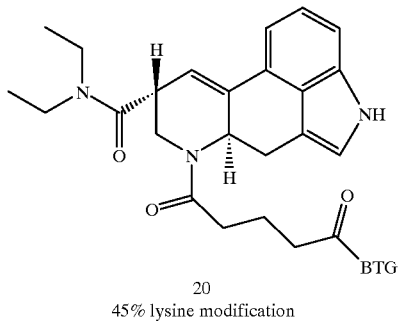

20
45% lysine modification

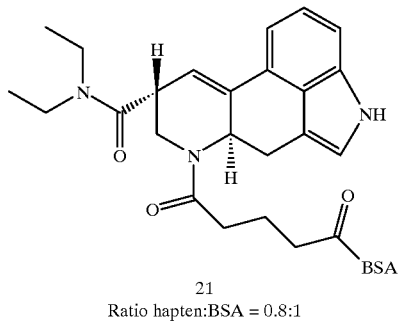

21
Ratio hapten:BSA = 0.8:1

The results in FIG. 3 indicate that free LSD competes with the BSA label-conjugate 21 for binding with the anti-LSD antibodies such that the presence of LSD results in a decrease (or inhibition) of the antibody-antigen binding. Thus, the LSD label-conjugate is useful as a reagent in the ELISA assay for the determination of LSD.

Another LSD hapten derived out of the piperidine nitrogen containing a biphenyl linker was also synthesized. The synthesis of this hapten is shown below in Scheme IV. Nor-LSD 16 was reacted with 3-iodopthalimide 2 in $K_2CO_3$ to yield compound 22. Hydrazinolysis provided the amine 23 which was further treated with linker 12 to provide the LSD hapten 24. The biphenyl linking group, which is more tolerable to light than monophenyl aliphatic linking groups, provides a more stable LSD derivative.

SCHEME IV

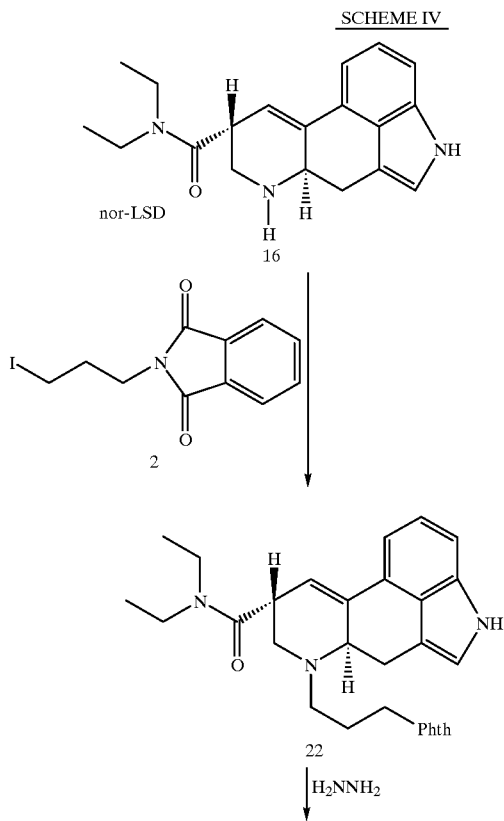

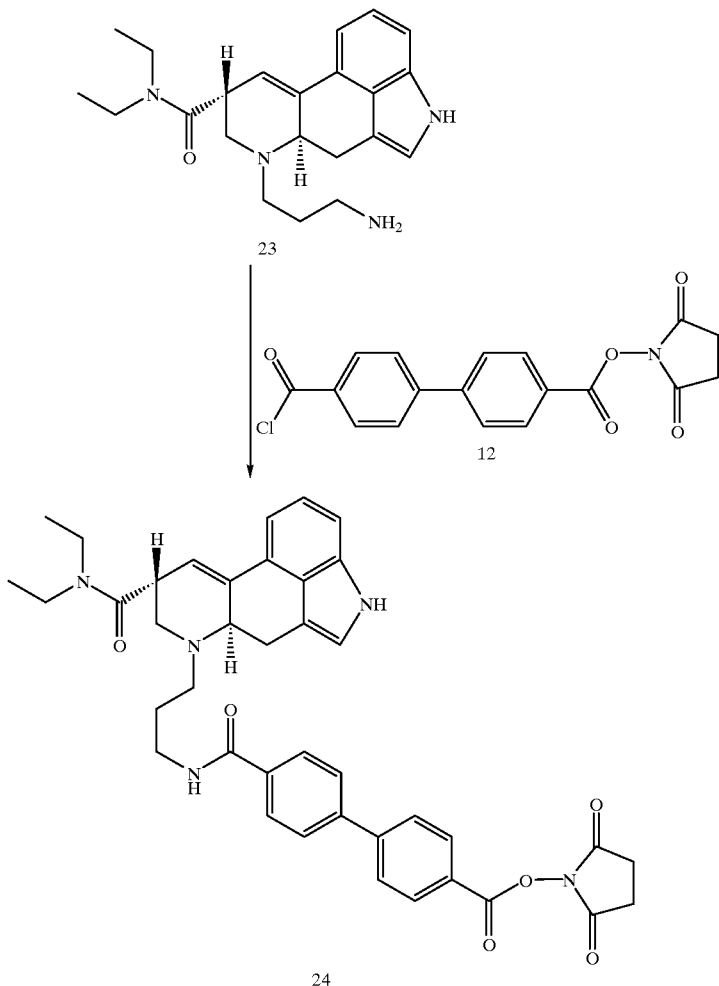

In addition to the preparation of N-aminopropyl nor-LSD 23, a carboxyalkyl functionalized at the nor-LSD nitrogen atom was also synthesized. The preparation of the resulting butyric acid derivative is described in Examples 24 and 25.

EXAMPLES

The following Examples shall serve to further illustrate the embodiments of the present invention without intending in any way to limit the scope of the invention. The numerical designations of the compounds in the headings of Examples 1–25, within the Examples, in FIGS. 1–3 and in the detailed description refer to the structural formulae shown in Schemes I–IV.

Example 1

Synthesis of D-lysergic acid diethyl amide 1

A mixture of 4.0 g (0.015 mol) of D-lysergic acid and 200 mL of dry DMF, under argon, was treated with 3.6 g (0.022 mol) of carbonyl diimidazole and stirred at room temperature for 1 hour. The reaction was treated with 15.2 mL (0.15 mol) of diethylamine and stirred at room temperature overnight. The reaction was concentrated at reduced pressure. The residue was taken up in 250 mL of $CH_2Cl_2$ and washed with 250 mL of $H_2O$. Insoluble material was removed by filtration and the layers were separated. The organic portion was washed with 250 mL of saturated brine solution, dried over anhydrous $Na_2SO_4$ and concentrated at reduced pressure. The residue was chromatographed on 500 g of silica gel using 3% $CH_3OH$ in $CH_2Cl_2$ as eluent to yield 3.65 g (75.7%) of D-LSD $[\alpha]_D=+50.4°$ (c=1%; $CHCl_3$) as a light brown amorphous solid. The 8α-epimer (also known as iso-LSD) has $[\alpha]_D=+226°$ (c=1%; $CHCl_3$).

Example 2

Synthesis of N-(3-iodopropyl)phthalimide 2

A solution of 10.0 g (0.04 mol) of N-(3-bromopropyl)-phthalimide in 240 mL of acetone was treated with 41.7 g (0.25 mol) of potassium iodide and stirred at room temperature for 4 days. The reaction mixture was filtered and the filtrate was diluted with 800 mL of ether and filtered again through celite. The filtrate was then concentrated at reduced pressure. The resulting yellow solid was recrystallized from 550 mL of hexane (filtered hot and boiled down to 300 mL) to yield 10.71 g (91.1%) of 2 as off-white needles.

Example 3

Synthesis of N-(4-iodobutyl)phthalimide 3

A solution of 5.0 g (0.018 mol) of N-(4-bromobutyl) phthalimide in 116 mL of acetone was treated with 20.7 g (0.125 mol) of potassium iodide and stirred at room temperature for 5 days. The reaction was filtered and the filtrate was diluted with 400 mL of ether, then filtered again through celite. The filtrate was concentrated at reduced pressure. The resulting solid was recrystallized from 300 mL of hexane (filtered hot and boiled down to 150 mL) to yield 4.0 g (68.6%) of 3 as white needles.

Example 4

Synthesis of 1-[3-(1,3-dihydro-1,3-dioxo-2 H-isoindol-2-yl)butyl]-N,N-diethyl]-D-lysergamide 4

A solution of 2.0 g (6.18 mmol) of D-LSD in 40 mL of dry THF under argon was cooled to −78° C. in a dry ice acetone bath. The solution was treated with 6.0 mL of 1.6 M n-butyllithium followed by 20 mL of dimethylpropyl urea and stirred at −78° C. for 15 minutes. The reaction mixture was treated with a solution of 3.0 g (9.1 mmol) of N-(4-iodobutyl)phthalimide 3 in 6 mL of N,N'-dimethylpropylene urea and stirred at −78° C. for 2 hours, then at room temperature for 90 minutes. The reaction mixture was concentrated at reduced pressure to an oil. The oil was diluted with 100 mL of ethyl acetate and washed with 5×50 mL of $H_2O$, dried over anhydrous sodium sulfate and concentrated at reduced pressure. The residue was chromatographed on 400 g of silica gel using 3% methanol in methylene chloride as eluent to yield 900 mg of 4 as a yellow amorphous solid and 800 mg of slightly less pure material for a combined yield of 52%.

Example 5

Synthesis of 1-(3-aminobutyl)-N,N-diethyl-D-lysergamide 5

A solution of 900 mg (1.7 mmol) of 4 in 25 mL of methanol was treated with 0.385 mL (12.3 mmol) of anhydrous hydrazine and stirred at room temperature overnight. The reaction mixture was concentrated at reduced pressure. The residue was treated with 25 mL of a mixture of 9:1 methylene chloride-methanol and the insoluble solids were filtered off. The filtrate was chromatographed on 200 g of silica gel using 25% methanol in methylene chloride as eluent to elute front running impurities, then 2% triethylamine 25% methanol in methylene chloride as eluent to elute the product to yield 563 mg (83%) of 5 as a yellow amorphous solid.

Example 6

Synthesis of 4-isothiocyanatobenzoyl chloride 6

A mixture of 500 mg (2.79 mmol) of 4-carboxyphenylisothiocyanate and 5 mL of thionyl chloride was refluxed for 6 hours. The reaction mixture was concentrated at reduced pressure and the resulting tan solid was pumped at high vacuum overnight. The solid was triturated with a small amount of hexane and collected by suction filtration to yield 516 mg (93%) of 6 as an off-white solid.

Example 7

Synthesis of 1-[[[(4-isothiocyanatophenyl)carbonyl]amino]butyl]-N,N-diethyl-D-lysergamide 7

A solution of 370 mg (0.94 mmol) of 5 in 15 mL of dry THF was cooled to 0° C. and treated with a solution of 190 mg (0.96 mmol) of 6 in 5 mL of dry THF, stirred at 0° C. for 30 minutes and then at room temperature overnight. The reaction mixture was treated with 0.14 mL (1.0 mmol) of triethylamine and stirred at room temperature for 2 hours The reaction mixture was concentrated at reduced pressure. The residue was dissolved in methylene chloride, washed with $H_2O$, dried over anhydrous sodium sulfate and concentrated at reduced pressure. The residue was chromatographed on 200 g of silica gel using 3% methanol in methylene chloride as eluent to yield 325 mg (62%) of 7 as a tan amorphous solid $[\alpha]_D=+47.5°$ (c=0.91%; $CHCl_3$).

Example 8

Synthesis of 1-[[[(4-thioureaphenyl)carbonyl]amino]butyl]-N,N-diethyl-D-lysergamide-BTG 8

A solution of 698 mg of BTG in 20 mL of 50 mM phosphate buffer pH 7.5 was cooled to 0° C. and treated with 58 mL of DMSO added dropwise very slowly over a 2 hour period. The mixture was treated with a solution of 90 mg (0.16 mmol) of 7 in 2 mL of DMSO added dropwise very slowly. The reaction mixture was stirred at room temperature for 18 hours, poured into a dialysis bag of 50 K cutoff, and dialyzed as follows: 2 liters of 75% DMSO in 50 mM KPi pH 7.5 for 2 hours at room temperature; 2 liters of 50% DMSO in 50 mM KPi pH 7.5 for 2 hours at room temperature; 2 liters of 30% DMSO in 50 mM KPi pH 7.5 for 2 hours at room temperature; 2 liters of 15% DMSO in 50 mM KPi pH 7.5 for 2 hours at room temperature; and 4×4 liters of 50 mM KPi pH 7.5 for 6 hours each at 4° C. The resulting conjugate was filtered through a 0.22 micron sterile filter to yield 116 mL of the LSD-BTG conjugate 8. The protein concentration as determined by Coomasie blue protein assay was 5.3 mg/mL. TNBS assay showed a 63.8% modification of available lysines on BTG.

Example 9

Synthesis of 1-[3-(1,3-dihydro-1,3-dioxo-2 H-isoindol-2-yl)propyl]-N,N-diethyl-D-lysergamide 9

A solution of 3.57 g (0.011 mol) of D-LSD in 70 mL of dry THF under argon was cooled to −78° C. in a dry ice acetone bath. The solution was treated with 6.7 mL of 2.5 M n-butyl lithium followed by 35 mL of N-N'-dimethylpropyleneurea and was stirred at −78° C. for 15 minutes. The reaction mixture was treated with a solution of 5.4 g (0.017 mol) of N-(3-iodopropyl)phthalimide 2 in 10 mL of N,N'-dimethylpropyleneurea and stirred at −78° C. for 90 minutes, then at room temperature for 2 hours The THF was removed at reduced pressure. The oil was diluted with 200 mL of ethyl acetate, washed with 5×100 mL of $H_2O$, dried over anhydrous sodium sulfate and concentrated at reduced pressure. The residue was chromatographed on 500 g of silica gel using 3% methanol in methylene chloride as eluent to yield 1.5 g of product as an amorphous solid. Mixed fractions were combined and rechromatographed twice on 250 g of silica gel to yield an additional 0.6 g of product for a combined yield of 2.1 g (37.5%) of 9.

Example 10

Synthesis of 1-(3-aminopropyl)-N,N-diethyl-D-lysergamide 10

A solution of 2.1 g (4.1 mmol) of 9 in 35 mL of methanol was treated with 0.92 mL (29.3 mmol) of anhydrous hydrazine and stirred at room temperature overnight. The reaction was concentrated at reduced pressure. The residue was diluted with 25 mL of methylene chloride, undissolved solids were filtered off, and the filtrate was chromatographed on 300 g of silica gel using 15% methanol in methylene chloride as eluent to remove front running impurities, then 2% triethylamine and 15% methanol in methylene chloride as eluent to elute the product to yield 1.24 g (79.5%) of 10 as a yellow amorphous solid.

Example 11

Synthesis of 1,1'-biphenyl-4,4'-dicarbonyl chloride 11

A mixture of 2.0 g (8.2 mmol) of 4,4'-biphenyldicarboxylic acid in 40 mL of dry THF was treated with 5.0 mL (55.0 mmol) of oxalyl chloride followed by 0.02 mL of dry DMF. The reaction was stirred at room temperature for 10 minutes, then heated to reflux for 90 minutes. The reaction mixture was concentrated at reduced pressure to a yellow oil. This was recrystallized from a mixture of THF and ether to yield 1.67 g (73%) of 11 as yellow needles.

Example 12

Synthesis of 4'-[[(2,5-dioxo-1-pyrrolidinyl)oxy]carbonyl][1,1'-biphenyl]-4-carbonyl chloride 12

A solution of 1.67 g (6.0 mmol) of 11 in 65 mL of dry THF was treated with 710 mg (6.17 mmol) of N-hydroxysuccinimide, followed by 0.835 mL (6.0 mmol) of triethylamine. The reaction was stirred at room temperature for 2 hours after which time it was filtered to remove triethylamine HCl. The filtrate was concentrated at reduced pressure to yield 2.0 g (93%) of 12 as a pale yellow solid.

Example 13

Synthesis of 1-[3-[[[4'-[[(2,5-dioxo-1-pyrrolidinyl)oxy]carbonyl][1,1'-biphenyl]-4-yl]carbonyl]amino]propyl]-N,N-diethyl-D-lysergamide 13

A solution of 850 mg (2.375 mmol) of 12 in 65 mL of dry THF under argon was cooled to 0° C. in an icebath, then treated with a solution of 900 mg (2.365 mmol) of 10 in 50 mL of dry THF and 0.6 mL (4.3 mmol) of triethylamine added dropwise over a 20 minute period. The reaction mixture was stirred at 0° C. for 1 hour, then warmed to room temperature, with stirring, for 1 hour. The mixture was concentrated at reduced pressure and the residue was dissolved in 100 mL of methylene chloride. The solution was washed with 100 mL of $H_2O$, 100 mL of saturated sodium bicarbonate solution, 100 mL of saturated brine solution, dried over anhydrous sodium sulfate and concentrated at reduced pressure to a brown residue. This was chromatographed on a short column of 100 g of silica gel using first methylene chloride as eluent, then 9:1 methylene chloride-ether as eluent to elute front running impurities, then 14:1 methylene chloride-isopropyl alcohol as eluent to elute the product to yield 650 mg (39%) of 13 as a cream colored solid $[\alpha]_D=+34.3°$ (c=0.45%; $CHCl_3$).

Example 14

Synthesis of 1-[[[3-carbonyl(1,1'-biphenyl-4-yl]carbonyl]-aminopropyl]D-lysergamide-BSA 14

The LSD hapten was dissolved in 100% DMF at a concentration of 5 mg/mL, and was added to a BSA solution to a final concentration of 200 µg LSD derivative/mL, 20 mg BSA/mL and 20% DMF in 50 mMKPi, pH 7.5. This conjugate was then dialyzed in dialysis tubing with MW cutoff of 25,000 daltons under two conditions (1) 20% DMF/50 mM KPi, pH 7.5, 10 fold dialysis followed by 10% DMF/50 mM KPi, pH 7.5, 10 fold dialysis and 0% DMF/50 mM Kpi pH 7.5, $10^3$ fold dialysis. (2) 20% DMF/50 mM KPi pH 7.5 $10^2$ fold dialysis followed by 10% DMF/50 mM Kpi, pH 7.5, $10^2$ fold dialysis and 0% DMF/50 mM Kpi, pH 7.5, $10^3$ fold dialysis. The number of LSD molecules per BSA in the LSD-BSA conjugate was determined by measuring the fluorescence of the LSD-biphenyl-BSA conjugate 14. The fluorescence of non-drug-BSA at the same BSA concentration as the LSD-biphenyl-BSA conjugate 14 was also recorded. The LSD-biphenyl-derivative 13 was used as a fluorescence standard. The concentration of BSA was determined with ROCHE total protein (product order number 44903/44026) using 50 mg/mL native BSA as standard.

Example 15

Synthesis of 8β-6-cyano-9,10-didehydro-N,N-diethylergoline-8-carboxamide 15

A refluxing solution of 3.0 g (28.3 mmol) of cyanogen bromide in 200 mL of dry chloroform under argon was treated with a solution of 2.0 g (6.2 mmol) of 1 (D-LSD) in 100 mL of dry chloroform added dropwise over a 20 minutes period. The reaction mixture was refluxed for 1 hour, then cooled to room temperature. The reaction mixture was washed twice with 100 mL of 1% aqueous tartaric acid solution. The combined aqueous washes were extracted once with 50 mL of chloroform. Both organic portions were combined and dried over anhydrous sodium sulfate and concentrated at reduced pressure to a black residue. This was chromatographed on 250 g of silica gel using ethyl acetate as eluent to yield 1.5 g (73%) of 15 as a pale yellow amorphous solid.

Example 16

Synthesis of 8β-9,10-didehydro-N,N-diethylergoline-8-carboxamide 16 and 8α-9,10-didehydro-N,N-diethylergoline-8-carboxamide 17

A mixture of 1.2 g (3.6 mmol) of 15, 2.1 g (32.1 mmol) of zinc dust, 11 mL of acetic acid and 2.1 mL of $H_2O$ was heated to reflux under argon for 4 hours The reaction mixture was cooled and decanted from the zinc residue, then concentrated at reduced pressure to a small volume. The concentrate was diluted with 10 mL of $H_2O$ and basified to pH 9 with concentrated ammonium hydroxide with cooling in an ice bath. The resulting gummy precipitate was extracted with 4×50 mL of methylene chloride. After the first extraction, an additional amount of concentrated ammonium hydroxide was added to readjust the pH to 9. The combined organic extracts were dried over anhydrous sodium sulfate and concentrated at reduced pressure. The residue was chromatographed on 150 g of silica gel using 10% methanol in acetone as eluent to yield 500 mg (45%) of 16 (nor-LSD) as a light brown amorphous solid, and 200 mg (18%) of 17 (nor iso-LSD) as a light brown amorphous solid. Also obtained was 400 mg of a mixture of both epimers. 16: $[\alpha]_D=+34.3°$ (c=0.455%; $CHCl_3$); 17: $[\alpha]_D=+208.9°$ (c=1.37%; $CHCl_3$).

Example 17

Synthesis of 5-[(2,5-dioxo-1-pyrrolidinyl)oxy]-5-oxo-pentanoyl chloride 18

A solution of 10.0 g (0.088 mol) of glutaric anhydride in 50 mL of dry THF under argon was treated with 10.0 g (0.087 mol) of N-hydroxysuccinimide and heated to reflux for 3.5 hours. The reaction was concentrated at reduced pressure to an oil. The oil was crystallized from 50 mL of ethyl acetate to yield 9.2 g (46%) of 5-[(2,5-dioxo-1-pyrrolidinyl)oxy]-5-oxo-pentanoic acid which was treated with 16 mL of thionyl chloride and heated at 45° C. for 3 hours under argon. The reaction mixture was concentrated at reduced pressure to a white solid which was triturated with a small amount of ether and collected by suction filtration. The product was dried overnight at high vacuum to yield 8.7 g (88%) of 18 as a white solid.

Example 18

Synthesis of 1-[[5-[8β-9,10-didehydro-8-[(diethyl-amino)carbonyl]ergolin-6-yl]-1,5-dioxopentyl]oxy]-2,5-pyrrolidinedione 19

A solution of 200 mg (0.65 mmol) of 16 in 10 mL of dry THF, under argon, was treated with 161 mg (0.65 mmol) of 18, followed by 0.2 mL (1.4 mmol) of dry triethylamine. The reaction mixture was stirred at room temperature for 30 minutes, then concentrated at reduced pressure. The residue was dissolved in methylene chloride, washed with $H_2O$ and saturated aqueous sodium bicarbonate solution, dried over anhydrous sodium sulfate and concentrated at reduced pressure to yield 330 mg (98%) of 19 as a yellow amorphous solid.

Example 19

Synthesis of 5-[8β-9,10-didehydro-8-[(diethyl-amino)carbonyl]ergolin-6-yl-1,5-dioxopentyl-BTG 20

A solution of 700 mg of BTG in 13 mL of 50 mM phosphate buffer pH 7.5 was cooled to 0° C. and treated with 13 mL of DMSO added dropwise very slowly. After the addition was complete, a solution of 84 mg (0.16 mmol) of 19 in 1 mL of DMSO was added dropwise very slowly. The reaction mixture was stirred at room temperature for 18 hours, poured into a dialysis bag of 50 K cutoff, and dialyzed as follows: 2 liters of 50% DMSO in 50 mM KPi pH 7.5 for 2 hours at room temperature; 2 liters of 25% DMSO in 50 mM KPi pH 7.5 for 2 hours at room temperature; 2 liters of 100% 50 mM KPi pH 7.5 for 2 hours at room temperature; and 7×4 liters 50 mM KPi pH 7.5 for 6 hours each at 4° C. The resulting conjugate was filtered through a 0.22 micron sterile filter to yield the LSD-BTG conjugate 20. The protein concentration as determined by Coomasie blue protein assay was 12.1 mg/mL. TNBS assay showed a 45% modification of available lysines on BTG.

Example 20

Synthesis of 5-[8β-9,10-didehydro-8-[(diethyl-amino)carbonyl]ergolin-6-yl- 1,5-dioxopentyl-BSA 21

A solution of 1.1 g of BSA in 22 mL of 50 mM phosphate buffer pH 7.5 was cooled to 0° C. and treated with 22 mL of DMSO added dropwise very slowly. After the addition was complete, 4 mL was removed and held aside as a reference. To the remaining 40 mL (1 g of BSA) was added dropwise a solution of 12 mg (0.02 mmol) of 19 in 0.5 mL of DMSO. The reaction mixture was stirred at room temperature for 18 hours, poured into a dialysis bag of 50 K cutoff, and dialyzed as follows: 2 liters of 50% DMSO in 50 mM KPi pH 7.5 for 2 hours at room temperature; 2 liters of 25% DMSO in 50 mM KPi pH 7.5 for 2 hours at room temperature; 2 liters of 100% 50 mM KPi pH 7.5 for 2 hours at room temperature; 7×4 liters of 50 mM KPi pH 7.5 for 6 hours each at 4° C. The resulting conjugate was filtered through a 0.22 micron sterile filter to yield the LSD-BSA conjugate 21. The protein concentration as determined by Coomasie blue protein assay was 14.6 mg/mL. The ratio of hapten/BSA was 0.8.

Example 21

Synthesis of 8β-9,10-didehydro-6-[3-(1,3-dihydro-1,3-dioxo-2 H-isoindol-2-yl)propyl]-N,N-diethylergoline-8-carboxamide 22

A solution of 568 mg (1.84 mmol) of 16 in 17 mL of dry DMF was treated with 413 mg (4.2 mmol) of anhydrous potassium carbonate followed by 653 mg (2.1 mmol) of N-(3-iodopropyl)-phthalimide 2 and stirred at 40° C. overnight. The reaction mixture was concentrated at reduced pressure, the residue was diluted with methylene chloride, washed with $H_2O$, dried over anhydrous sodium sulfate and concentrated at reduced pressure. The product was then chromatographed on 150 g of silica gel using ethyl acetate as eluent to yield 833 mg (91%) of 22 as a yellow amorphous solid.

Example 22

Synthesis of 8β-6-(3-aminopropyl)-9,10-didehydro-N,N-diethylergoline-8-carboxamide 23

A solution of 820 mg (1.65 mmol) of 22 in 30 mL of methanol was treated with 0.4 mL (12.7 mmol) of anhydrous hydrazine and stirred at room temperature overnight. The reaction mixture was filtered and concentrated at reduced pressure. The residue was chromatographed on 100 g of silica gel using 2% triethylamine-15% methanol in methylene chloride as eluent. Fractions containing product were combined and rechromatographed on 150 g of silica gel using 2% triethylamine-15% methanol in chloroform as eluent to yield 560 mg (93%) of 23 as a yellow amorphous solid.

Example 23

Synthesis of 1-[[[4'-[[[3-[8β-9,10-didehydro-8-[(diethyl-amino)carbonyl]ergolin-6-yl]propyl]amino] carbonyl][1,1'-biphenyl]-4-yl]carbonyl]oxy]-2,5-pyrrolidinedione 24

A solution of 1.32 g (3.7 mmol) of 12 in 50 mL of dry methylene chloride under argon was cooled to 0° C. and treated with a solution of 535 mg (1.46 mmol) of 23 in 50 mL of dry methylene chloride added dropwise over a 30 minute period. After the addition was complete, the reaction mixture was washed with saturated aqueous sodium bicarbonate solution, dried over anhydrous sodium sulfate and concentrated in vacuo. The residue was chromatographed on 100 g of silica gel using 5% isopropyl alcohol as eluent. Fractions containing product were combined and concentrated at reduced pressure to a yellow solid. The solid was taken up in ether and concentrated five times to remove residual isopropyl alcohol to yield 280 mg (28%) of 24 as a yellow solid.

Example 24

Synthesis of 8β-6-butyric acid ethyl ester-9,10-didehydro-N,N-diethylergoline-8-carboxamide 25

A solution of 1.1 g (3.5 mmol) of 16 in 35 mL of dry DMF under argon was treated with 800 mg of anhydrous potassium carbonate, followed by 2 mL of ethyl bromo butyrate, stirred at 40° C. for 6 hours, then at room temperature overnight. The reaction mixture was concentrated at reduced pressure. The residue was diluted with methylene chloride, washed with $H_2O$, dried over anhydrous sodium sulfate and concentrated at reduced pressure. The residue was chromatographed on 200 g of silica gel using ethyl acetate as eluent to yield 780 mg (52%) of 25, the 8β-epimer, as a yellow amorphous solid. Also obtained were 84 mg of the 8α-epimer and 395 mg of a mixture of 8α- and 8β- epimers.

Example 25

Synthesis of 8β-6-butyric acid-9,10-didehydro-N,N-diethylergoline-8-carboxamide 26

A solution of 400 mg (0.94 mmol) of 25 in 16 mL of methanol and 8 mL of $H_2O$ was treated with 1.6 g of potassium carbonate and stirred at room temperature for 3 days. The reaction mixture was poured into a separatory funnel and diluted with 50 mL of methylene chloride and 50 mL of $H_2O$. The aqueous layer was neutralized with 6 N HCl to pH 7. The mixture was shaken vigorously in the separatory funnel. The layers were separated and the aqueous portion was extracted 2 more times with methylene chloride. The combined organic extracts were dried over anhydrous sodium sulfate and concentrated at reduced pressure to yield 330 mg (88%) of 26 as a tan solid.

Example 26

Animal Immunization Protocol

The immunogen was mixed 1:1 with Freunds adjuvant. Five goats each received multiple site injections across the back as follows:

| 1st week | Complete Freunds | 1.0 mg | Across back |
| 2nd week | Incomplete | 1.0 mg | Across back |
| 3rd week | Incomplete | 1.0 mg | Across back |
| 4th week | Incomplete | 1.0 mg | Across back |
| 8th week | Incomplete | 0.5 mg | Across back |
| Monthly | Incomplete | 0.5 mg | Across back |

Six months after the animals received the appropriate immunogen, a test bleed was obtained and the antisera was evaluated in the ELISA microtiter plate assay using the appropriate LSD-BSA conjugate as the plate coating material described as follows in Example 27.

Example 27

ELISA microtiter plate assay for LSD using anti-LSD antibodies and LSD-BSA label-conjugates.

High binding 96 well polystyrene microtiter plate wells (Costar, MA) were coated with 50 μL each of a LSD-BSA conjugate (diluted in PBS azide buffer pH 7.2) and allowed to incubate for 2 hours at room temperature or overnight at 2° C. to 8° C. The plates were washed 3× with the PBS buffer. 100 μL of 1% BSA in PBS azide buffer was dispensed into each well and the plate was incubated for 2 hours at room temperature. The plates were washed 3× with the PBS containing 0.05% TWEEN-20 (Sigma). 50 μL of LSD or nor-LSD diluted in BSA-PBS azide buffer, or 50 μL of 1% BSA-PBS azide buffer without the drug as a control, was added. 50 μL of the appropriate antisera in 1% BSA-PBS azide buffer was added to each well. The plates were incubated for 1 hour at 37° C., then washed 3× with PBS-TWEEN-20. 50 μL of anti-goat-alkaline phosphatase conjugate (Fisher Scientific) was added to each well and the plate was incubated for 1 hour at 37° C. The plate was washed 3× with PBS-TWEEN-20 buffer and 50 μL of p-nitrophenylphosphate (Sigma) was added to each well. The plates were incubated for 30 minutes at room temperature. The reaction was stopped by the addition of 50 μL of 3 N NaOH and the resulting optical density was measured using a microtiter plate reader at a wavelength of 405 nm. The data generated in the assays is presented below. The resulting inhibition or displacement curves for LSD are shown in FIGS. 1–3.

The data resulting in inhibition curve of FIG. 1:

| Conc(ng/mL) | G648(OD) | G651(OD) |
|---|---|---|
| 0 | 1.05 | 1.17 |
| 0.5 | 0.8 | 1.05 |
| 1 | 0.33 | 0.75 |
| 5 | 0.25 | 0.39 |

The data resulting in inhibition curve of FIG. 2:

| Nor-LSD(ng/mL) | G651(OD) |
|---|---|
| 0 | 1.38 |
| 1 | 1.2 |
| 5 | 0.88 |
| 5(LSD) | 0.63 |

The data resulting in inhibition curve of FIG. 3:

| Conc(ng/mL) | G651(OD) | G648(OD) |
|---|---|---|
| 0 | 0.67 | 0.7 |
| 0.5 | 0.5 | 0.52 |
| 1 | 0.33 | 0.37 |
| 5 | 0.19 | 0.17 |

What is claimed is:

1. The compound having the structure;

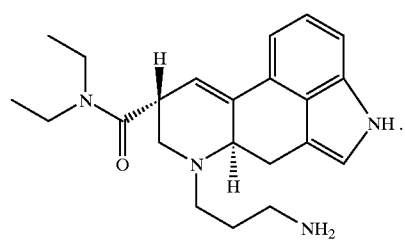

2. The compound having the structure;
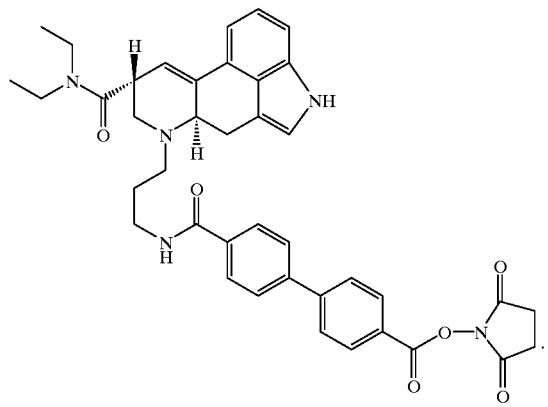
3. The compound having the structure;
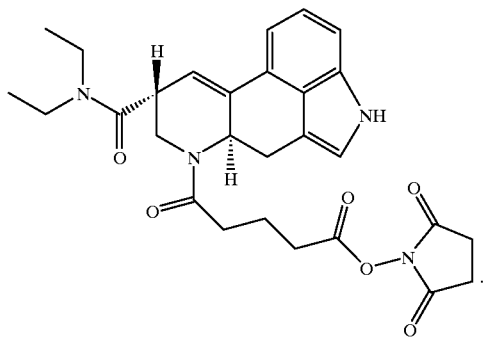
4. The compound having the structure;
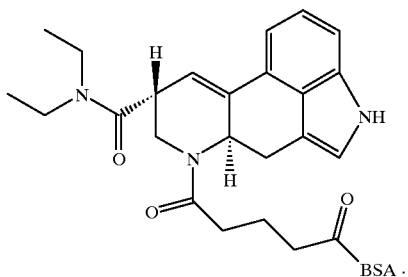
5. The compound having the structure;
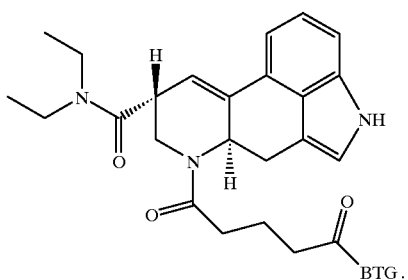
* * * * *